US007354597B2

(12) United States Patent
Johnson et al.

(10) Patent No.: US 7,354,597 B2
(45) Date of Patent: Apr. 8, 2008

(54) MICROSCALE LYOPHILIZATION AND DRYING METHODS FOR THE STABILIZATION OF MOLECULES

(75) Inventors: Audrey M. Johnson, Cambridge, MA (US); Michael J. Cima, Winchester, MA (US); Robert S. Langer, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 770 days.

(21) Appl. No.: 10/308,579

(22) Filed: Dec. 3, 2002

(65) Prior Publication Data

US 2004/0043042 A1 Mar. 4, 2004

Related U.S. Application Data

(60) Provisional application No. 60/336,793, filed on Dec. 3, 2001.

(51) Int. Cl.
*A61F 2/02* (2006.01)
*A61K 9/14* (2006.01)

(52) U.S. Cl. ....................................... 424/426; 424/489

(58) Field of Classification Search ..................... None
See application file for complete search history.

(56) References Cited

U.S. PATENT DOCUMENTS

| | | | |
|---|---|---|---|
| 4,521,975 | A | 6/1985 | Bailey |
| 4,531,373 | A | 7/1985 | Rubinsky |
| 4,770,856 | A | 9/1988 | Uthemann et al. |
| 5,031,336 | A | 7/1991 | Diesner et al. |
| 5,797,898 | A | 8/1998 | Santini, Jr. et al. |
| 6,123,861 | A | 9/2000 | Santini, Jr. et al. |

(Continued)

FOREIGN PATENT DOCUMENTS

EP 0 569 115 A2 11/1993

(Continued)

OTHER PUBLICATIONS

Arakawa et al., "Factors affecting short-term and long-term stabilities of proteins," *Advanced Drug Delivery Reviews* 10:1-28 (1993).

(Continued)

*Primary Examiner*—Carlos A. Azpuru
(74) *Attorney, Agent, or Firm*—Sutherland Asbill & Brennan LLP

(57) ABSTRACT

Methods and systems are provided for microscale lyophilization or microscale drying of agents of interest, such as pharmaceutical agents or other molecules that are unstable or easily degraded in solution. The drying method includes (a) providing a liquid comprising an agent of interest dissolved or dispersed in a volatile liquid medium; (b) depositing a microquantity (between 1 nL and 10 μL) of the liquid onto a preselected site of a substrate; and then (c) drying the microquantity by volatilizing the volatile liquid medium to produce a dry, solid form of the agent of interest. The lyophilization method includes freezing the microquantity of liquid after step (b) and before step (c). By processing the agent of interest in microquantities in controlled contact with a substrate surface, improved heat and mass transfer is provided, yielding better process control over drying of the agent of interest compared to conventional bulk drying or lyophilization.

40 Claims, 4 Drawing Sheets

U.S. PATENT DOCUMENTS

| | | | | |
|---|---|---|---|---|
| 6,264,990 | B1 | 7/2001 | Knepp et al. | |
| 6,267,958 | B1 | 7/2001 | Andya et al. | |
| 6,322,994 | B1 | 11/2001 | Reid | |
| 6,444,226 | B1 | 9/2002 | Steiner et al. | |
| 6,491,666 | B1 | 12/2002 | Santini, Jr. et al. | |
| 6,527,762 | B1 | 3/2003 | Santini, Jr. et al. | |
| 6,562,065 | B1 | 5/2003 | Shanley | |
| 6,808,522 | B2 * | 10/2004 | Richards et al. | 604/890.1 |
| 7,056,338 | B2 | 6/2006 | Shanley | |
| 2002/0107470 | A1 | 8/2002 | Richards et al. | |
| 2002/0151776 | A1 | 10/2002 | Scheidt et al. | |
| 2002/0183721 | A1 | 12/2002 | Santini, Jr. et al. | |
| 2003/0068355 | A1 | 4/2003 | Shanley | |
| 2005/0058684 | A1 | 3/2005 | Shanley | |
| 2006/0177564 | A1 | 8/2006 | Diaz | |

FOREIGN PATENT DOCUMENTS

| | | |
|---|---|---|
| WO | WO 01/07107 | 2/2001 |
| WO | WO 01/64344 | 9/2001 |

OTHER PUBLICATIONS

Cleland, et al., "The development of stable protein formulations: a close look at protein aggregation, deamidation, and oxidation," *Crit. Rev. Ther. Drug Carrier Systems* 10: 307-77 (1993).

Ha, et al., "Peroxide Formation in Polysorbate 80 and Protein Stability," *J. Pharma, Sci.* 91(10):2252-64 (2002).

* cited by examiner

MICROSCALE LYOPHILIZATION AND DRYING METHODS FOR THE STABILIZATION OF MOLECULES

CROSS-REFERENCE TO RELATED APPLICATIONS

Priority is claimed under 35 U.S.C. § 119 to U.S. provisional application Ser. No. 60/336,793, filed Dec. 3, 2001.

Statement Regarding Federally Sponsored Research or Development

This invention was made with government support under Grant No. 1-R24-AI47739-03 awarded by the National Institutes of Health. The government has certain rights in the invention.

BACKGROUND OF THE INVENTION

This invention relates to methods for the controlled handling and storage of unstable proteins or other molecules and the improved production, filling, and storage of dry forms of such molecules.

Many useful proteins and other molecules that are unstable in aqueous solutions are handled and stored in a dry powder form. Bulk drying and lyophilization (freeze-drying) are known, useful ways to stabilize protein structure and activity. Traditional freeze-drying methods involve the freezing of an aqueous solution containing various stabilizing agents, followed by application of a vacuum to remove the water by sublimation, producing a dry powder that is relatively stable and suitable for long-term storage. Lyophilization, such as in the manufacture of a variety of pharmaceutical products, typically is conducted by filling a vessel, such as vial or ampule, with an aqueous solution of the product pharmaceutical, and then placing the vial in a refrigerated tray within a lyophilizer. Optionally the filled vial is first frozen in a separate chamber before being placed into the lyophilizer. Actual practice demands that many vials are placed within an aseptic lyophilizer for simultaneous processing. Lyophilization, however, can be difficult to optimize, particularly with vial-to-vial uniformity. Processing difficulties include determining what process conditions (i.e. cycle) to use, and then ensuring that each vial experiences exactly the same processing conditions. One of the primary sources of these problems is heat transfer, which is difficult to achieve in a vacuum—such as the vacuum chamber of the lyophilizer. It would be advantageous to improve the heat transfer in lyophilization processes.

In some cases, lyophilization is better than drying protein formulations, because it avoids exposing the formulation to capillary forces associated with evaporation from a liquid to a gas phase. In other cases, however, the damage to proteins from lyophilization, caused by freezing and sublimation, may exceed the damage due to evaporation, and a drying technique thus may be preferable. Nevertheless, evaporation from bulk solutions is generally slow and formulation components often degrade during the drying process as they are concentrated in the solution. It would be advantageous to provide methods for preparing stable, dry powder forms of proteins and other molecules that reduce the disadvantages associated with bulk drying and/or lyophilization.

Powder filling technologies, however, are not as well developed as liquid filling methods, and the amount of powder deposited in a particular container can be difficult to measure and control. For example, dry powders frequently are sensitive to packing forces, static charge, moisture, and other variables that can affect the handling of the powder. Such variables can make it difficult to reproduce or deliver precise quantities, particularly microquantities, of the powders. It therefore would be advantageous to provide methods for improving the accuracy of handling precise quantities of dry powders.

It therefore would be desirable to provide improved methods for obtaining stable, dry powder forms of proteins and other molecules. In addition, it would be desirable to provide methods for delivering precise quantities of dry proteins and other molecules to preselected sites. It would also be desirable to provide microscale reservoirs containing a pharmaceutical formulation that will be stable over long periods.

SUMMARY OF THE INVENTION

Improved methods for preparing dry, stable forms of proteins or other molecules have been developed. The methods utilize microscale lyophilization or microscale drying, depending upon the particular molecules (agents of interest) being processed. In one embodiment, the method comprises the steps of: (a) providing a liquid which comprises an agent of interest dissolved or dispersed in a volatile liquid medium; (b) depositing a microquantity of the liquid onto a preselected site of a substrate; and then (c) drying the microquantity by volatilizing the volatile liquid medium to produce a dry, solid form of the agent of interest. In another embodiment, the method comprises the steps of: (a) providing a liquid which comprises an agent of interest dissolved or dispersed in a volatile liquid medium; (b) depositing a microquantity of the liquid onto a preselected site of a substrate; (c) freezing the microquantity of liquid; and then (d) drying the microquantity by volatilizing the volatile liquid medium to produce a dry, solid form of the agent of interest. The microquantity is a volume between 1 nL and 10 μL, preferably between 1 nL and 1 μL, more preferably between 10 nL and 500 nL. By processing the agent of interest in microquantities in controlled contact with a substrate surface, improved heat and mass transfer is provided, yielding better process control over drying of the agent of interest compared to conventional bulk drying or lyophilization. This can provide better dried product, particularly for example for molecules that are unstable or easily degraded in solution, such as is the case with certain proteins for example.

In one embodiment, the agent of interest comprises a pharmaceutical agent. In one embodiment, the pharmaceutical agent comprises a peptide or a protein. In another embodiment, the pharmaceutical agent is selected from glycoproteins, enzymes, hormones, interferons, interleukins, and antibodies. In yet another embodiment, the pharmaceutical agent is selected from vaccines, gene delivery vectors, antineoplastic agents, antibiotics, analgesic agents, and vitamins. The agent of interest optionally may further comprise one or more pharmaceutically acceptable excipients. In still other embodiments, the agent of interest is selected from small molecules, amino acids, peptides, and proteins (e.g., enzymes), any of which are for use in non-pharmaceutical applications.

In one embodiment, the volatile liquid medium comprises a solvent for the agent of interest and the liquid of step (a) comprises a solution of the active agent dissolved in the solvent. In another embodiment, the volatile liquid medium comprises a non-solvent for the agent of interest and the liquid of step (a) comprises a suspension of the active agent dispersed in the non-solvent. The volatile liquid medium can be aqueous or non-aqueous. A non-aqueous volatile liquid medium may comprise, for example, an aprotic, hydrophobic, non-polar liquid, such as one including biocompatible perhalohydrocarbons or unsubstituted saturated hydrocarbons.

The preselected site on the substrate can be essentially any solid surface suitable for holding the microquantity of liquid. In one embodiment, the preselected site is a microscale reservoir. In another embodiment, two or more, preferably 100 or more, preselected sites, which can be in the form of microscale reservoirs, are provided on a single substrate. In one embodiment, the microscale reservoirs can be provided in a microchip device.

In one embodiment of the microscale lyophilization process, the drying step can include reheating the frozen microquantity. In another embodiment of either microscale drying or microscale lyophilization, the drying step can include subjecting the microquantity to a sub-atmospheric pressure. In yet another embodiment, the drying step is carried out at a temperature at or less than 10° C. at the preselected site.

In another aspect, bulk quantities of a stable, dry form of an agent of interest are produced by using the present microscale drying and lyophilization methods, particularly in a continuous process, to produce numerous, discrete microquantities that are then combined to form said stable dry bulk quantities of the agent, for subsequent use or packaging.

In another aspect, a pharmaceutical formulation is provided which comprises a dry, solid form of a pharmaceutical agent made by the present microscale drying and lyophilization methods. The pharmaceutical formulation can include one or more excipients that undergo the microscale lyophilization or microscale drying process with the pharmaceutical agent, or alternatively, said one or more excipients can be combined with the pharmaceutical agent after microscale processing.

In still another aspect, a medical device is provided which contains a dry, solid form of a pharmaceutical agent made by the present microscale drying and lyophilization methods. In one embodiment, the medical device (e.g., a microchip device) is implantable and comprises microscale reservoirs containing the pharmaceutical agent. The pharmaceutical agent can undergo microscale lyophilization or microscale drying in the microscale reservoirs of the medical device, or alternatively can be loaded into the microscale reservoirs following microscale processing at another site. In the former case, the in situ drying or lyophilization allows each reservoir to be filled with a more controlled amount of solid agent of interest than filling of the reservoir with a pre-lyophilized or dried powder. It can thus provide more uniform, more controllable packing density of a solid form of the agent of interest.

In yet another aspect, an apparatus is provided for using the microscale methods to produce a dry, solid form of an agent of interest. In one embodiment, the apparatus includes (i) a supply means for providing a liquid which comprises an agent of interest dissolved or dispersed in a volatile liquid medium; (ii) a deposition means for depositing two or more discrete microquantities of the liquid onto two or more discrete preselected sites, respectively, of a substrate; (iii) a dryer means for drying the microquantity by volatilizing the volatile liquid medium to produce a dry, solid form of the agent of interest; (iv) a collection means for removing the dry, solid form of the agent of interest from the preselected sites and then combining together the two or more microquantities of dry, solid form of the agent of interest; and (iv) a conveying means for returning the preselected sites and substrate from the collection means, following the removal of the dry, solid form of the agent of interest, to the deposition means so that additional two or more discrete microquantities of the liquid can be deposited onto the two or more discrete preselected sites of the substrate. This apparatus can further include a cooling means for freezing the deposited two or more discrete microquantities of liquid at the two or more discrete preselected sites, before drying. Optionally, the apparatus can further include a heating means for re-heating the frozen microquantities during the drying of the microquantities.

DETAILED DESCRIPTION OF THE INVENTION

Figure 1:
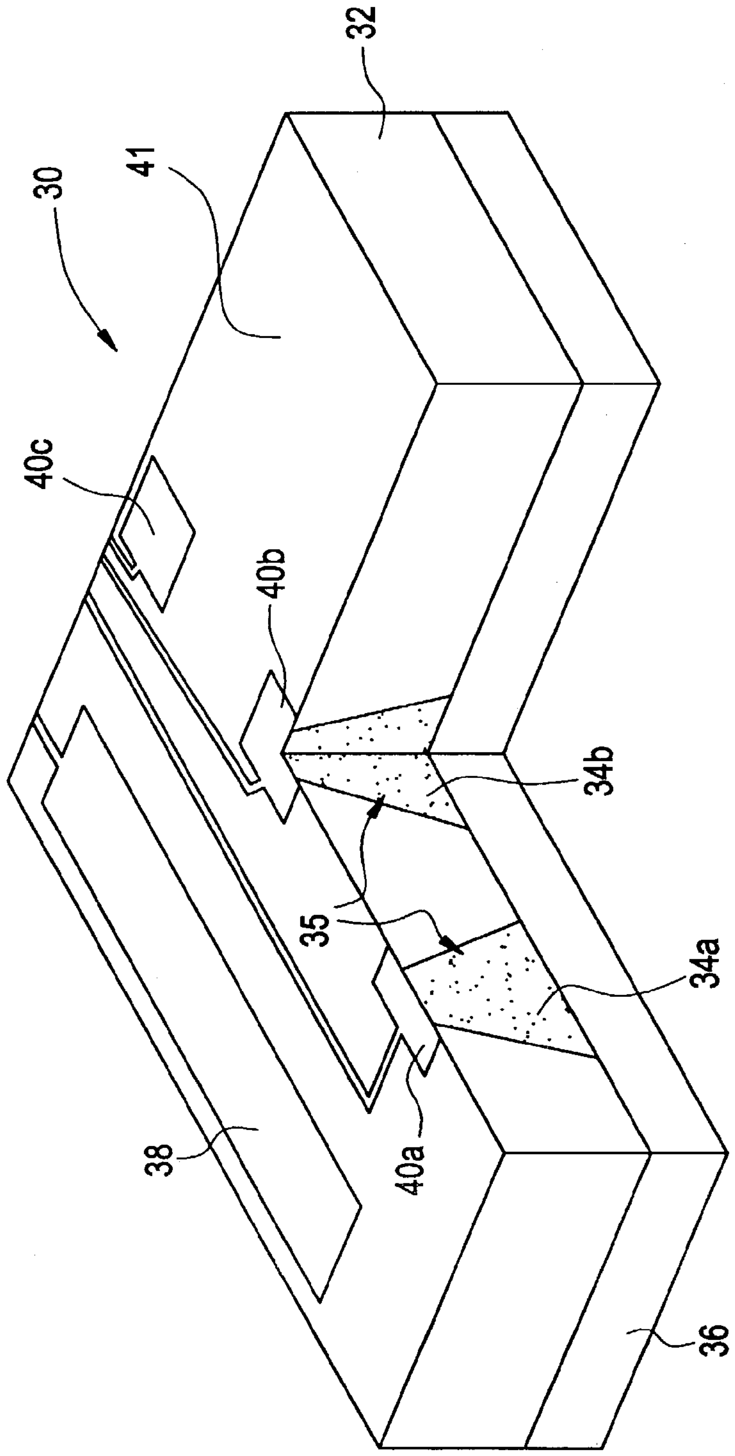
FIG. 1 is a perspective and cross-sectional view of a typical microchip device used for controlled release of drugs or other types of molecules.

Drying and lyophilization methods have been adapted to microscale processing in order to enhance stability and/or activity of unstable molecules and to facilitate precise filling and handling of microquantities of dry, solid forms of molecules (i.e. agents of interest). In addition, microscale lyophilization and microscale drying in reservoirs has the advantage of reproducibility and simplicity as compared to filling microscale reservoirs with pre-lyophilized or dried powders. The concentration of substances in the injected solution, as well as the volume of the solution injected, may be precisely controlled.

As used herein, the term "microquantity" refers to small volumes between 1 nL and 10 μL. The microquantity preferably is between 1 nL and 1 μL, more preferably between 10 nL and 500 nL.

As used herein, the term "dry, solid form" includes powders, crystal, microparticles, amorphous and crystalline mixed powders, monolithic solid mixtures, and the like. The solid form may be a free-flowing powder, an agglomerated "cake", or some combination thereof.

The Drying and Lyophilization Methods

The microscale methods (i.e. microscale lyophilization or microscale drying) for obtaining a dry, solid form of an agent of interest preferably are as follows: The drying method includes (a) providing a liquid comprising an agent of interest dissolved or dispersed in a volatile liquid medium; (b) depositing a microquantity of the liquid onto a preselected site of a substrate; and then (c) drying the microquantity by volatilizing the volatile liquid medium to produce a dry, solid form of the agent of interest. The lyophilization method includes freezing the microquantity of liquid after step (b) and before step (c). The term "drying"

refers to removal of the liquid solvent or non-solvent, by evaporation, sublimation, or a combination thereof.

The preselected site on the substrate can be essentially any solid surface suitable for holding the microquantity of liquid. It typically should be a good thermal conductor and non-reactive with the agent of interest and with the volatile liquid medium. In one embodiment, the preselected site is a microscale reservoir. In another embodiment, two or more, preferably 100 or more, preselected sites, which can be in the form of microscale reservoirs, are provided on a single substrate. In one embodiment, the microscale reservoirs can be provided in a microchip device. As used herein, the term "microscale reservoir" refers to a concave-shaped solid structure suitable for containing a liquid material and of a size and shape suitable for filling with a microquantity of liquid (comprising the agent of interest) and for removal of the dry, solid form of the residual agent of interest. In one embodiment, the microscale reservoir has a volume of less than 100 μL (e.g., less than 75 μL, less than 50 μL, less than 25 μL, less than 10 μL, etc.) and greater than about 1 nL (e.g., greater than 5 nL, greater than 10 nL, greater than about 25 nL, greater than about 50 nL, greater than about 1 μL, etc.). The dimensions of the microscale reservoir can be selected to maximize or minimize contact area between the liquid and the surrounding surface of the microscale reservoir. Microscale reservoirs can be fabricated in the substrate using any suitable fabrication technique known in the art, including MEMs processes. The surface of the substrate and/or of the microscale reservoirs optionally can be treated or coated to alter one or more properties of the surface. Examples of such properties include, but are not limited to, hydrophilicity/hydrophobicity, surface roughness, electrical charge, release characteristics, and the like.

Lyophilization

The microscale lyophilization process preferably comprises three steps: deposition, freezing, and drying. In the first step, the liquid comprising the agent of interest is deposited at the preselected site of the substrate. Examples of suitable deposition methods include injection and ink-jet printing. In the second step, the liquid is cooled to a temperature below the freezing point of the volatile liquid medium, causing the liquid to freeze. For many pharmaceutical agents of interest, the lyophilization process temperature is between about −20 and −40° C. This may be achieved by contacting the substrate with a cold sink, such as a chilled metal block, by placing the substrate in a chilled container, conducting the process in a cold enough environment, or by other means known in the art for removing heat from a contained liquid. In the final step, the frozen liquid is placed under vacuum and the moisture is sublimed, leaving at the preselected site a dry, solid form of the agent of interest. The process advantageously should yield a stable and reproducible amount of the agent of interest.

In an optional embodiment, the final step includes heating the frozen liquid/partially sublimated solid (above the freezing point of the liquid) to further remove the volatilizable liquid medium by evaporation. For example, there could be a primary drying step by sublimation (e.g., at 100 mtorr, material surface temperature of −40° C.) followed by a secondary drying step with some heating (e.g., at 100 mtorr, material surface temperature of −25° C.).

The process equipment that can be adapted for carrying out the microscale lyophilization is known in the art. A typical lyophilizer consists of a chamber for vacuum drying, a vacuum source, a freezing mechanism, a heat source, and a vapor removal system. For some agents of interest (e.g., pharmaceutical agents), the vacuum pressure in the lyophilization process is as low as 0.1 mm Hg.

Drying

For drying, the process consists of two steps: deposition and drying. This is equivalent to the lyophilization process described above, without the freezing step. Drying can be done at ambient or elevated pressures and temperatures for some agents of interest, but preferably is done such that the microquantity is at sub-atmospheric pressure and/or a temperature of 10° C. or less, particularly for thermally labile agents of interest.

Selection of Lyophilization or Drying

Bulk instability of an agent of interest is time dependent. Therefore, microscale drying has the advantage of a high evaporation rate compared to bulk drying due to the small volumes of solution involved, and therefore may prevent damage to the agent of interest. In the microscale processes, the surface area of droplets is high compared to the droplet volume, which makes the process much faster (smaller time constant). The intimate contact between the solution and the reservoir surface also aids in heat transfer to the drying or lyophilizing material. Heat transfer is required to supply the energy of vaporization. Such efficient heat transfer is not offered by methods as spray drying where the heat transfer is supplied by vapor contact. The speed of the process is more important for molecules (e.g., certain enzymes or other proteins) that degrade more quickly in solution, i.e. where bulk denaturation or bulk instability factors predominate. However, the high surface area may be detrimental for those molecules that are more susceptible to denaturation at surfaces (whether solid surfaces or gas/liquid interfaces). Surface area denaturation is not time dependent. When comparing lyophilization results to drying results, an important factor is the susceptibility of the molecule to damage from capillary forces (during drying) versus the susceptibility to damage from freezing and sublimation.

Another feature distinguishing lyophilization and drying is the surface area of the dry product material after processing. The surface area can be critical to the rate of redissolution of the dry material. The lyophilized material, if processed correctly, has a high surface area, whereas the dried material is substantially lower, due to compaction of the material, which results from capillary forces acting on the material during standard drying. A compacted powder has a lower surface area, which can dramatically reduce its dissolution rate in comparison to the lyophilized powder. Therefore, one important factor in selecting between lyophilization and drying could be, and likely is, the desired properties, such as dissolution rate, of the final product.

From the teachings herein, one skilled in the art can select or readily determine the appropriate method for the particular protein or molecule of interest, as there is significant literature on the stability of various proteins and other complex biomolecules under different conditions. For many common biomolecules, there exist data which describe individual protein/biomolecule stabilities under various conditions and which list recommended excipients and surfactants for processing. The susceptibility of many biomolecules to freezing damage, sublimation damage, and drying damage is also documented in the literature. The effectiveness of different lyoprotectants and cryoprotectants has been extensively studied, and from these data one skilled in the art should be able to determine whether lyophilization or drying would be better for particular biomolecules, as well as which excipients should be added to the solution.

As illustrated in the Examples below, the susceptibility of biomolecules to surface denaturation may vary. The high surface area to volume ratio of the microscale processes described herein makes the surface denaturation processes potentially significant. As the susceptibility of various biomolecules to surface denaturation is documented to some extent for different biomolecules, one skilled in the art can anticipate that surface denaturation likely is significant if the literature indicated that during bulk processing it was necessary to add surfactant or if it is important to prevent foaming during mixing—where the surface area of a bulk solution is greatly increased. In other words, the surface effects can be due to (1) interactions with the solid surface, and/or (2) interactions with the air/liquid interface, particularly present with bubbles. Surfactants can mitigate one or both of these interactions. One skilled in the art also could examine whether surfactants are necessary during spray drying of the biomolecule in order to anticipate a possible need for surfactant during microscale drying or lyophilization. This would particularly be true under the likely circumstance that the spray drying involves a higher air interface to volume ratio than the microscale drying and lyophilization process.

The Agent of Interest

A wide variety of substances can serve as or be included as part of the agent of interest. As used herein, the term "agent of interest" refers to the one or more materials that comprise the dry, solid material yielded by the microscale lyophilization or microscale drying processes described herein.

In a preferred embodiment, the agent of interest comprises a pharmaceutical agent. The pharmaceutical agent can be a therapeutic, prophylactic, or diagnostic agent. The therapeutic, prophylactic, or diagnostic agent can be provided in a pure form or combined with one or more pharmaceutically acceptable excipient. The pharmaceutical agent can comprise small molecules, large (i.e. macro-) molecules, or a combination thereof. In one embodiment, the large molecule agent of interest is a protein or a peptide. Examples of suitable types of proteins include, but are not limited to, glycoproteins, enzymes (e.g., proteolytic enzymes), hormones (e.g., LHRH, steroids, corticosteroids), antibodies, cytokines (e.g., α-, β-, or γ-interferons), interleukins (e.g., IL-2), and insulin. In various other embodiments, the pharmaceutical agent can be selected from vaccines, gene delivery vectors, antineoplastic agents, antibiotics, analgesic agents, and vitamins.

In one exemplary embodiment, the agent of interest comprises parathyroid hormone (PTH). As used herein, "PTH" includes the complete human hormone (hPTH 1-84); fragments of the hormone responsible for bone growth promotion, such as hPTH 1-34 and hPTH 1-38, and analogs in which the amino acid sequence is modified slightly, yet retain bone growth promotion properties, such as PTH-RP; and synthetic and/or recombinant biologically active peptide derivatives of parathyroid hormone (e.g., hPTH (1-28)), such as described in U.S. Pat. No. 6,417,333 to Bringhurst et al. The PTH may be native or synthesized by chemical or recombinant means. In forming a pharmaceutical formulation the PTH could be microscale processed in a salt form, such as a chloride or acetate (e.g., as hPTH(1-34)Cl or PTH(1-34)OAc) without excipient, or alternatively, the PTH could be microscale processed with an excipient (e.g., polyethylene glycol having a molecular weight between about 100 and 10,000 Daltons) that promotes re-dissolution of the PTH upon administration or delivery to a patient. In another embodiment, the microscale processed (i.e. dry) PTH could be (re-)suspended with a non-aqueous excipient vehicle suitable for stable storage.

In still other embodiments, the agent of interest comprises catalysts (e.g., zeolites, enzymes), reagents, tag or marker molecules (e.g., radiolabels, fluorophores, and the like), fragrances, and flavoring agents, which are useful in non-pharmaceutical applications.

The methods described herein are particularly useful for processing agents of interest that comprise molecules that are unstable in solution. The term "unstable in solution" refers to molecules that may undergo reaction or structural or conformational changes that render them unsuitable for an intended use. Examples of the types of mechanisms inducing these changes include self-degradation, aggregation, deamidation, oxidation, cleavage, refolding, hydrolysis, conformational changes, and other chemical mechanisms. For example, proteolytic enzymes are known to undergo autolysis. As another example, some proteins form aggregates or undergo deamidation. Non-proteins also may be unstable. Vitamin C, for example, is known to degrade in aqueous solution.

The time the enzyme, protein, or other molecule spends in solution during processing therefore may be highly critical. The difference between a bulk process and a microscale process is thus significant, as the period spent in solution differs widely. One advantage of the present method is therefore to enable the agent of interest to be in solution a shorter time. This small time-constant of microscale processes reduces the degradation of the biomolecule due to degradation in the solution.

One skilled in the art can reference the literature for the protein or biomolecule of interest to identify or estimate the agent's susceptibility to degradation under different conditions. See, for example, Arakawa, et al. "Factors affecting short-term and long-term stabilities of proteins." *Advanced Drug Delivery Reviews* 10:1-28 (1993); and Cleland, et al. "The development of stable protein formulations: a close look at protein aggregation, deamidation, and oxidation." *Crit. Rev. Ther. Drug Carrier Systems* 10:307-77 (1993).

The agent of interest may be processed with one or more additives. Examples of such additives include, but are not limited to, surfactants, lyoprotectants, and cryoprotectants. Selection of an appropriate additive will depend on the particular agent of interest and drying/lyophilization process to be used. In one embodiment, such additives comprise a pharmaceutically acceptable excipient. The term "pharmaceutically acceptable excipient" refers to any non-active ingredient of the formulation intended to facilitate delivery and administration by the intended route. The pharmaceutically acceptable excipient may enhance handling, stability, solubility, and dispersibility of the active agent. The choice and amounts of excipient for a particular formulation depend on a variety of factors and can be selected by one skilled in the art. Examples of these factors include the type and amount of pharmaceutical agent, the particle size and morphology of the solid form of the agent(s) of interest, and the desired properties and route of administration of the final formulation. Examples of types of pharmaceutically acceptable excipients include bulking agents, wetting agents, stabilizers, crystal growth inhibitors, antioxidants, antimicrobials, preservatives, buffering agents, surfactants, dessicants, dispersants, osmotic agents, binders (e.g., starch, gelatin), disintegrants (e.g., celluloses), glidants (e.g., talc), diluents (e.g., lactose, dicalcium phosphate), color agents, flavoring agents, sweeteners, and lubricants (e.g., magnesium stearate, hydrogenated vegetable oils) and combinations thereof. Other suitable pharmaceutically acceptable excipients include most carriers approved for parenteral administration, including water, saline, Ringer's solution, Hank's solution, and solutions of glucose, lactose, dextrose, mannitol, ethanol, glycerol, albumin, and the like.

The Volatile Liquid Medium

The agent of interest can be combined with, or generated in, a suitable volatile liquid medium to form a solution or suspension of the agent of interest, using techniques known in the art.

As used herein, the "volatile liquid medium" refers to a liquid vehicle in which the agent of interest is provided before/for undergoing microscale lyophilization or microscale drying. It may be a solvent or a non-solvent for the agent of interest, and it can be volatilized (e.g., by evaporation or sublimation or a combination thereof) to leave the dissolved or suspended agent of interest. The selection of the volatile liquid medium depends, at least in part, the chosen agent of interest and the desired conditions of lyophilization or drying (e.g., temperature, pressure, speed of volatilization, etc.). The volatile liquid medium preferably is selected to minimize its reaction with the agent of interest and to avoid promoting degradation of the agent of interest before the liquid medium can be volatilized.

In one embodiment, the volatile liquid medium comprises a solvent for the agent of interest so that the liquid vehicle comprises a solution of the active agent dissolved in the solvent. In another embodiment, the volatile liquid medium comprises a non-solvent for the agent of interest so that the liquid vehicle comprises a suspension of the active agent dispersed in the non-solvent.

The volatile liquid medium may aqueous or non-aqueous. Examples of aqueous volatile liquid media include, but are not limited to, water, saline, Ringer's solution, Hank's solution, and aqueous solutions of glucose, lactose, dextrose, mannitol, ethanol, glycerol, albumin, and the like. Examples of non-aqueous volatile liquid media include, but are not limited to, anhydrous, aprotic, hydrophobic, non-polar liquids, as described in U.S. Pat. No. 6,264,990 to Knepp et al., which is incorporated herein by reference (and which describes biocompatible perhalohydrocarbons or unsubstituted saturated hydrocarbons, such as perfluorodecalin, perflurobutylamine, perfluorotripropylamine, perfluoro-N-methyldecahydroquindine, perfluoro-octohydro quinolidine, perfluoro-N-cyclohexylpyrilidine, perfluoro-N,N-dimethylcyclohexyl methylamine, perfluoro-dimethyl-adamantane, perfluorotri-methylbicyclo (3.3.1) nonane, bis(perfluorohexyl) ethene, bis(perfluorobutyl) ethene, perfluoro-1-butyl-2-hexyl ethene, tetradecane, methoxyflurane and mineral oil.).

Where the agent of interest comprises a pharmaceutical agent, it may be preferable for the volatile liquid medium to be pharmaceutically acceptable for parenteral administration. In other embodiments, such as non-pharmaceutical applications, essentially any volatile liquid media can be used, provided the other criteria described above are met.

The volatile liquid medium may include one or more additives, such as those described above. Examples of these additives include surfactants and other excipient materials. In one embodiment for preparing a stable protein formulation from a protein sensitive to air-liquid interfaces, the additive comprises a polyoxyethylene sorbitan fatty acid ester, particularly polyoxyethylene sorbitan monooleate (i.e. TWEEN™ 80, polysorbate 80). See Ha, et al., *J. Pharma. Sci.,* 91(10):2252-64 (2002).

Uses of the Methods

The methods for in situ lyophilization and drying of agents of interest described herein may be applied to any process in which the deposition of a small and precisely controlled amount of protein or other substances (i.e. other agents of interest) is required. Representative examples include loading devices with small amounts of an agent of interest. Such devices can be, for example, those suitable for use in drug discovery, medical diagnostic, various sensor applications, and drug delivery.

In one embodiment, a microscale reservoir or other storage vessel is filled with a pharmaceutical formulation (comprising a pharmaceutical agent that has undergone microscale lyophilization or microscale drying) that will be satisfactorily stable over an extended period (e.g., 2, months, 4, months, 6 months, 9 months, 12 months, etc.) The reservoir or medium then can be used in applications requiring small, precisely controlled amounts of the pharmaceutical formulation, such as delivery of a protein drug or other therapeutic molecule, for example.

In another embodiment, the methods are used in the loading of microscale reservoirs in a medical device. In one embodiment, the medical device is implantable, such as a drug delivery microchip device or medical stent. Alternatively, the microscale reservoirs are in other types of devices, such as for in vitro diagnostic testing or screening for biologically active molecules. Examples of microchip devices for controlled release and exposure of agents of interest from microscale reservoirs (for both medical and non-medical applications) are described in U.S. Pat. Nos. 5,797,898 and 6,123,861, both to Santini, et al., and PCT WO 01/64344, WO 01/41736, WO 01/35928, and WO 01/12157, which are hereby incorporated by reference in their entirety. FIG. 1 illustrates one embodiment of a microchip device 30, which includes substrate 32 having reservoirs 34*a* and 34*b*, which are loaded with agent of interest 35 that has been subject to microscale lyophilization or microscale drying. Anodic reservoir caps 40*a-c* cover the reservoirs at the release surface 41 and sealing plate 36 enclosed the reservoirs at the opposing surface. Application of an electric potential between a cathode 38 and one or more of the anodic reservoir caps causes the reservoir cap(s) to disintegrate and permit release of the agent of interest 35 from the reservoirs. The agent of interest 35 can be microscale lyophilized or dried in the reservoirs 34*a* and 34*b*, or loaded into these reservoirs after microscale lyophilization or drying at another site. In the latter case, the dry sold form of the agent of interest preferably is suspended in a liquid non-solvent and the resulting suspension loaded into the reservoirs. Before sealing the reservoirs, this liquid non-solvent can be removed (e.g., by volatilization) or can remain with the agent of interest.

In a preferred embodiment, the reservoirs of the microchip device contain a pharmaceutical formulation. The pharmaceutical formulation can consist entirely of the agent of interest that has undergone the microscale drying or lyophilization or alternatively can comprise one or more agents of interest that have undergone microscale drying or lyophilization and one or more other components that have not undergone microscale drying or lyophilization. In the latter case, the one or more other components can be added to the reservoirs before, after, or with the agents of interest that have undergone microscale drying or lyophilization. The agent of interest can undergo the microscale drying or lyophilization in the microchip reservoirs, or alternatively the microscale drying or lyophilization can be conducted at different preselected sites and then loaded into the microchip reservoirs. In the latter case, the agent of interest can be loaded as a dry powder, or more preferably, the microscale dried or lyophilized agent of interest is suspended in a liquid non-solvent and the resulting suspension can be accurately metered into the microchip reservoirs. The liquid non-solvent can remain as a liquid vehicle for the agent of interest or it can be removed (e.g., by evaporation) following transfer of the suspension into the microchip reservoirs.

The pharmaceutical formulation comprising microscale lyophilized or dried agent of interest can be loaded into a variety of implantable drug delivery device. The implantable drug delivery device could be a microchip device as described above, or it could be a medical stent having microfabricated reservoirs in the body of the stent, e.g., on its exterior surface, its interior surface, or loaded into apertures extending through the stent. Such a stent optionally could have a biodegradable or bioerodible coating over the surface(s) to protect the pharmaceutical formulation before and during implantation and/or to delay drug release. In other embodiments, the discrete microquantities of agent of interest could be combined following microscale processing and then loaded, in bulk, into other drug delivery devices (implantable or non-implantable), such as a dry powder inhaler.

In other embodiments, the reservoirs of the microchip device contain other, i.e. non-pharmaceutical, agents of interest. For example, the agent of interest could be a catalyst (e.g., zeolite, enzyme) or reagent useful in in vitro diagnostic testing, a fragrance molecule, or a beverage additive. Non-pharmaceutical agents of interest also can be loaded into various types of micro-reservoirs other than those found in microchip devices.

Figure 3:
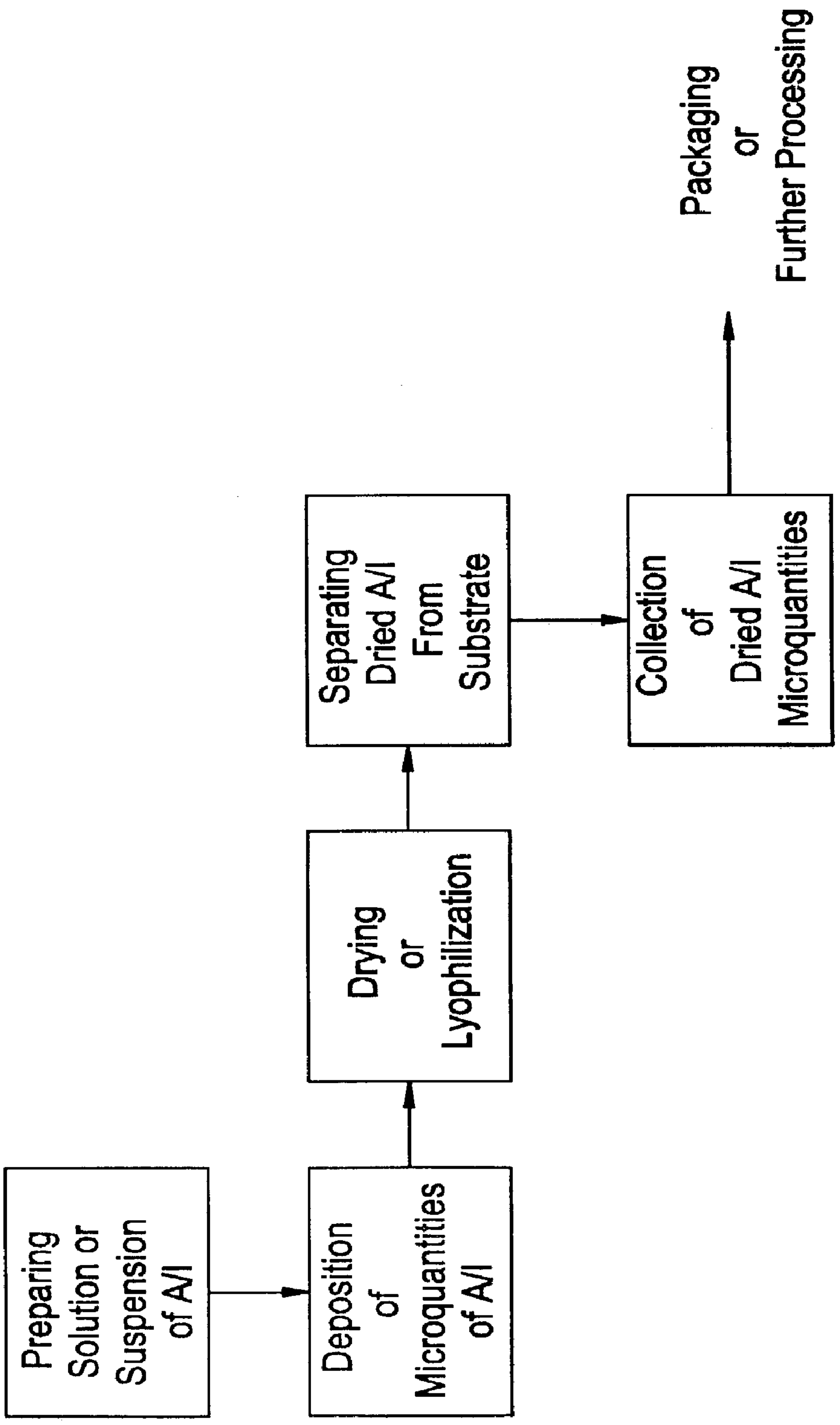
FIG. 3 is a block flow diagram of a continuous process for microscale lyophilization or drying of a material, wherein the discrete microquantities are collected together.

In another embodiment, the microscale drying and lyophilization methods are applied to prepare larger quantities (i.e. macroquantities) of dry forms of the agent of interest (A/I). See FIG. 3. For example, macroquantities of material can be prepared simply by simultaneously processing many filled reservoirs. Arrays of reservoirs can be filled with automated dispensing equipment followed by lyophilization or drying. The dried discrete microquantities of agent of interest can be combined following microscale processing and then packaged or used in bulk quantities in applications where needed. The agent of interest processed according to the microscale methods described herein could provide bulk quantities having greater stability, longer shelf life, and/or better activity than the same agent of interest that was bulk dried or bulk lyophilized.

In one embodiment, macroquantities quantities of material can be prepared simply by simultaneously processing numerous microquantities, for example, in arrays of filled microscale reservoirs. Arrays of reservoirs can be filled using automated dispensing equipment and then subjected to lyophilization or drying. Such arrays, preferably including hundreds or thousands of reservoirs or other preselected sites, can be provided in one or more substrates.

The use of microscale lyophilization typically facilitates very short cycle times, and allow for an entirely new approach to lyophilization, which is. different from current commercial processes. For example, a continuous or semi-continuous lyophilization process could include the use of a tape substrate with many microscale reservoirs in it, which would be made to move through a system that includes four stations: (1) dispensing, (2) freezing, (3) lyophilization, and (4) packaging. A similar approach could be used for microscale drying. The tape would move under an auto-fill station, which quickly dispenses a microquantity of a solution of the agent of interest, e.g., a protein, into the reservoirs. The tape would then move over a freezing mantle to freeze the contents of the reservoirs, and then move though a small slit partition into a vacuum chamber where lyophilization is completed. The tape exits the vacuum chamber through a second slit and moves to the packaging station, which can take several forms. For example, the tape can be cut in to sections, which are rolled into vials, e.g., such that the bottom surface of the tape is against the inside wall of the vial, thereby providing that the lyophilate will quickly dissolve when a quantity of saline solution is later introduced into the vial. Alternatively, the powder could be mechanically knocked off the tape or another substrate means into a vial or other collection container. Such powder removal techniques and mechanisms could include a vibration mechanism (e.g., with ultrasonic means) and/or a stretching means to elastically deform the tape or substrate to force the plugs of powder from the tape. In this or any other embodiment, the surface of the substrate or the surface of the preselected site(s) can be provided with a suitable release coating or otherwise pretreated to facilitate removal of the dry, solid form of the agent of interest from the site(s). For example, the surface could have a fluorinated polymer coating (e.g., a polytetrafluoroethylene) or another fluorinated coating (e.g., (trifluoro-1,1,2,2 tetrahyrooctyl)trichlorosilane. In another example, the surface could be a silanized surface, which would be similar or identical the surfaces of commercially available silanized glassware that is used for laboratory work with proteins.

Figure 4:
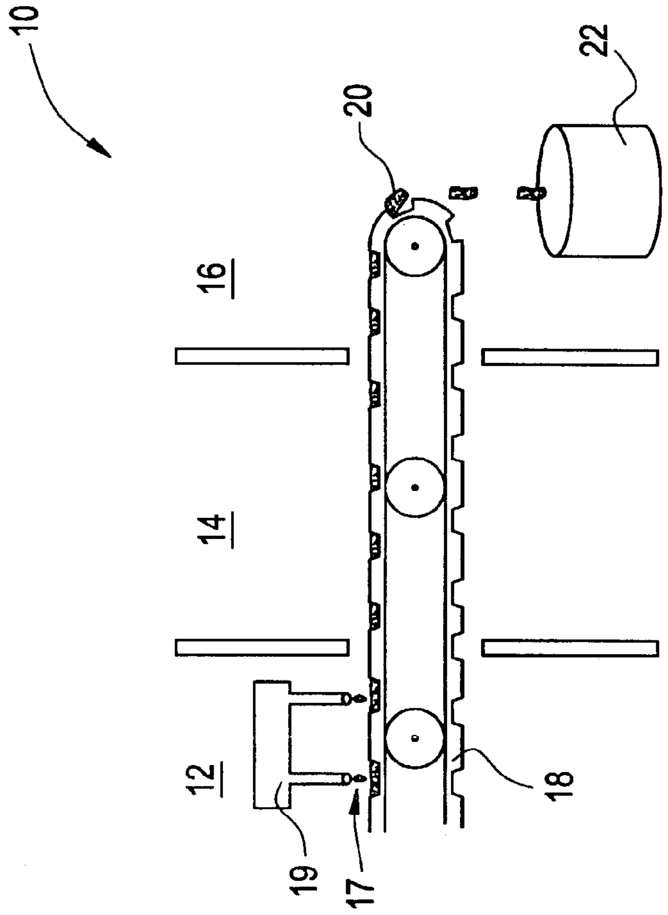
FIG. 4 is cross-sectional view of a conveyor system in one embodiment of a continuous process for microscale lyophilization or drying of a material.

One example of a continuous microscale process is illustrated in FIG. 4, where microscale processing system 10 includes a deposition zone 12, a drying or lyophilization zone 14, and a release and collection zone 16. A conveyor belt 18 comprises a plurality of reservoirs. Using a filling/deposition device 12, reservoirs are filled with a liquid 17, which comprises an agent of interest dissolved or dispersed in a volatile liquid medium in zone 12. As the conveyor belt 18 moves into zone 14, the volatile liquid medium is volatilized and removed from the reservoirs. The conveyor belt 18 moves into zone 16 and as the belt turns down, the dried microquantities of agent of interest 20 are ejected from the reservoirs and into collection vessel 22. The emptied reservoirs are then ultimately conveyed back to the deposition zone 12.

Employing such a scheme provides several advantages. First, a continuous process offers better process control over a batch process. Specifically, each reservoir will experience precisely the same conditions (e.g., temperature and pressure). In contrast, in currently available lyophilizers, an array of vials are lyophilized batchwise such that a vial in the center of the vacuum chamber undergoes a different cycle than vials near the edge of vacuum chamber, possibly leading to unacceptable variation in product quality. Second, each of the units typically will be much smaller than the batch system, thereby making aseptic design and operation much easier and less costly. Third, the development of the "right", or optimum, process conditions (for a particular product) is much easier, because smaller amounts of material are held up in the process. Thus, many tests can be done with much smaller amounts of material.

The present invention can best be understood with reference to the following non-limiting examples.

EXAMPLES

A series of experiments were performed in order to evaluate the effects of microscale drying and lyophilization on biological formulations. The microscale processes were performed on different protease enzymes and the activity of the enzyme before and after processing was evaluated. The enzymes tested were trypsin, collagenase, and elastase; these respectively degrade peptides, collagen, and elastin. The four processes studied for each enzyme were:

(I) Bulk drying—drying of a 2.5 mL solution of enzyme at room temperature;

(II) Microscale drying—drying of 30 nL droplets of enzyme solution in microchip reservoirs at room temperature;

(III) Bulk lyophilization—freezing, and then vacuum sublimation of a 2.5 mL solution of enzyme; and (IV) Microscale lyophilization—freezing, then vacuum sublimation of 30 nL droplets of enzyme solution in microchip reservoirs.

The activity of the enzyme after processing was measured using a fluorescent substrate assay technique, and compared to activity of unprocessed enzyme. The results are expressed as the percentage of the original activity remaining after processing. (If the processing had no effect, the result would be 100%; if the processing destroyed all activity, the result would be 0%.) Uncertainties are represented as the standard deviation.

Example 1

Lyophilization and Drying of Trypsin Solutions in a Microchip Reservoir

Figure 2A:
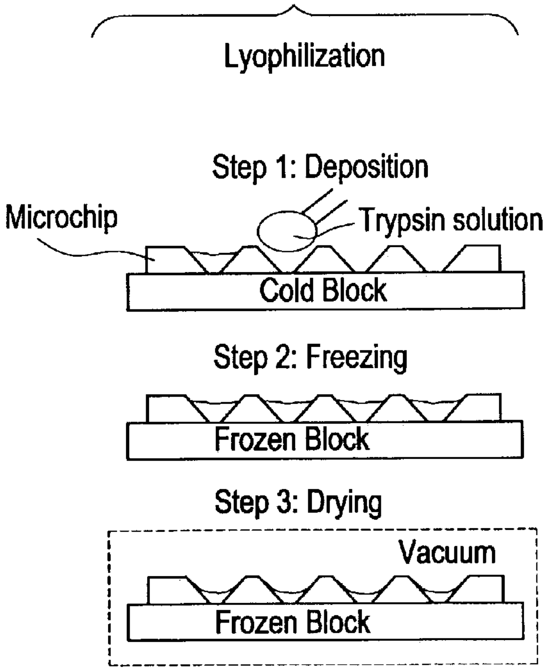
FIGS. 2A and 2B are illustrations of typical embodiments of the process steps for microscale lyophilization (FIG. 2A) and microscale drying (FIG. 2B).
Figure 2B:
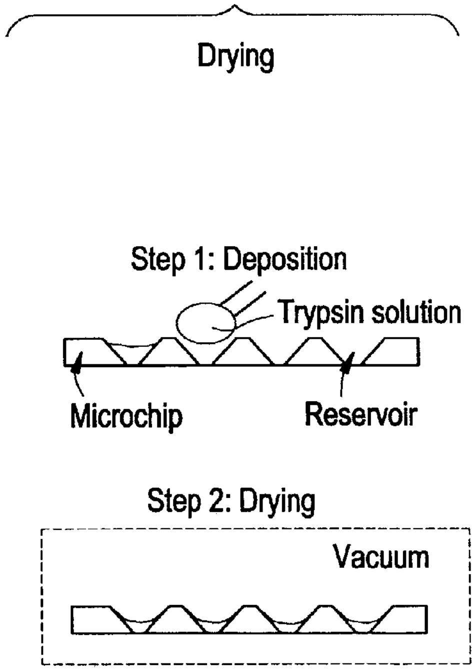

Trypsin solutions were injected and lyophilized or dried in microchip reservoirs. The activity of the enzyme was assayed to assess the effect of the processes on protein activity. The lyophilization and drying process steps are illustrated in FIG. 2A and FIG. 2B, respectively. The procedures were as follows:

In Situ Lyophilization Procedure

1. Prepared an aqueous solution containing 4 mg/mL trypsin, 0.0005% Tween-20, and 0.1M HC1 ("the trypsin solution");

2. Filled a 50 μL Luer-lock syringe with the trypsin solution and placed the syringe into a World Precision Instruments (WPI) microinjector (model number KITE-R);

3. Programmed the WPI microinjector pump controller (model number UMC4) with the desired injection volume and flow rate;

4. Placed a silicon microchip onto a cooled aluminum block (4° C.) on the stage of a light microscope;

5. Aligned the syringe needle tip with one of the reservoirs of the microchip and injected 30 nL of the trypsin solution into the reservoir;

6. Repeated the injection process for each reservoir to be filled (between 1 and 25 reservoirs per microchip);

7. Transferred the microchip to a frozen copper block (−20° C.) and allowed the solution in the reservoirs to freeze;

8. Placed the copper block with the microchip in a dessicator and applied a vacuum of approximately −8 psig (0.2 bar) to the dessicator container; and 9. Maintained the vacuum until the water from the solution had sublimed, and then stored the microchip under dry conditions.

The time between filling and freezing was minimized. Depending upon the number of reservoirs filled, the time was between 10 and 100 seconds.

The freezing and drying of the protein in the reservoirs was monitored by color change. A reservoir containing liquid trypsin solution appears black. When the solution freezes, it turns gray. When the solvent has sublimed, the reservoir appears empty except for a white residue, which is the dry protein. The change from frozen to sublimed was difficult to see while it was still in the dessicator, but by removing some samples from the dessicator, it was determined that sublimation occurred in less than five minutes.

In Situ Drying Procedure

1. Prepared an aqueous solution containing 4 mg/mL trypsin, 0.0005% Tween-20, and 0.1M HC1 ("the trypsin solution");

2. Filled a 50 μL Luer-lock syringe with the trypsin solution and placed the syringe into a WPI microinjector;

3. Programmed the WPI microinjector pump controller with the desired injection volume and flow rate;

4. Placed a clean silicon microchip onto a glass slide on the stage of a light microscope;

5. Aligned the syringe needle tip with one of the reservoirs of the microchip and injected 30 nL of the trypsin solution into the reservoir;

6. Repeated the injection process for each reservoir to be filled;

7. Placed the glass slide with the microchip in a dessicator and applied a vacuum of approximately −8 psig (0.2 bar) to the dessicator container;

8. Maintained the vacuum until the water from the solution had evaporated, and then stored the microchip under dry conditions.

The drying of the protein in the reservoirs was monitored by color change. A reservoir containing liquid trypsin solution appeared black. When the solvent had evaporated, the reservoir appeared empty except for a white residue. Complete evaporation took approximately 5-10 seconds.

Trypsin Activity Assay and Results

Trypsin activity assays were performed using BZAR (rhodamine 110, bis-(benzyloxycarbonyl-L-arginine amide), dihydrochloride) as a substrate for the enzyme. The enzyme converts the BZAR substrate into the fluorescent product rhodamine 110-benzyloxycarbonyl-L-arginine amide. Solutions containing a fixed amount of substrate and a range of enzyme concentrations were prepared and allowed to react for 10 minutes. The fluorescence of each solution was measured and plotted as a function of enzyme concentration. The slope of this curve, as given by the best-fit straight line, is proportional to the enzyme activity.

To compare the activity of the enzyme after processing to the activity pre-processing, the assay was performed on both unprocessed and processed enzyme. The percent difference between the slopes of the two curves obtained is equivalent to the percent of enzyme activity lost as a result of the processing. Assays were performed in triplicate.

Each assay solution contained 20 mM calcium chloride, 10 mM N-[2-hydroxyethyl]piperazine-N'-[2-ethanesulfonic acid], 0.0005% (v/v) Tween-20, 10% (v/v) dimethylsulfoxide, and 0.1 μg/mL BZAR in a 3 mL aqueous solution at pH 7.50. The enzyme concentrations tested were 0, 10, 30, 60, 100, 300, 600, and 1000 ng/mL. The reaction was allowed to proceed at 25° C. for 10 minutes. Fluorescence was recorded using a Photon Technology International (PTI) (model number R928/0115/0381) fluorometer with a Xenon short-arc lamp, a Products for Research Inc. photomultiplier tube, and a PTI photomultiplier detector. The excitation and emission wavelengths were 492 and 523 nm, respectively.

The results of the assays are shown in Table 1 below. The results indicate that the trypsin lyophilized using the method described above retained 74±0.7% of the original activity and that the trypsin dried using the method described above retained 88±1.7% of the original activity. For comparison, trypsin lyophilized in bulk as a 2.5 mL solution (not injected) retained 77±0.5% of the original activity. The process of bulk drying was not studied, because trypsin degrades so rapidly in solution (bulk drying takes approximately 36 hours, and the activity of trypsin solutions stored overnight is negligible). In summary, trypsin showed good preservation of activity during microscale drying, even better than the result of bulk lyophilization, which is the common method of preparation for this enzyme.

It is thought that the microscale drying is best because trypsin (i) degrades quickly in solution, making the process time constant critical; (ii) is not very susceptible to denaturation at surfaces, making the increased surface area of the microscale process unimportant; and (iii) is more susceptible to freezing and sublimation damage than capillary forces, making drying better than lyophilization.

Example 2

Lyophilization and Drying of Collagenase Solutions in a Microchip Reservoir

The in situ drying and lyophilization processes of Example 1 were repeated with collagenase, in place of trypsin, starting with a slightly different solution. For collagenase, the solution in Step 1 consisted of an aqueous solution containing 4 mg/mL collagenase and 0.0005% Tween-20. (No HCl was included.)

Collagenase activity assays were performed using GPLGP (rhodamine 110, bis-[glycine-proline-leucine-glycine-prolyl-amide]) as a substrate for the enzyme. The enzyme converts the GPLGP substrate into the fluorescent product rhodamine 110-glycine-proline-leucine-glycine-prolyl-amide. Solutions containing a fixed amount of enzyme and a range of substrate concentrations were prepared and allowed to react for 4 hours. The fluorescence of each solution was measured before and after the reaction and the difference plotted as a function of substrate concentration. Because the range of substrate concentrations was much less than the observed Michaelis-Menten constant for the reaction, the slope of this curve, as given by the best-fit straight line, is proportional to the enzyme activity.

To compare the activity of the enzyme after processing to the activity pre-processing, the assay was performed on both unprocessed and processed enzyme. The percent difference between the slopes of the two curves obtained is equivalent to the percent of enzyme activity lost as a result of the processing. Assays were performed in triplicate.

Each assay solution contained 20 mM calcium chloride, 10 mM N-[2-hydroxyethyl]piperazine-N'-[2-ethanesulfonic acid], 0.0005% (v/v) Tween-20, and 0.1 μg/mL collagenase in a 2 mL aqueous solution at pH 7.50. The substrate concentrations tested were 0, 0.015, 0.03, 0.06, 0.1, 0.25, 0.45, and 0.70 nmol/mL. The reaction was allowed to proceed at 37° C. for 4 hours. Fluorescence was recorded using a Photon Technology International (PTI) fluorometer with a Xenon short-arc lamp, Products for Research Inc. photomultiplier tube and PTI photomultiplier detector. The excitation and emission wavelengths were 492 and 523 nm, respectively. The results of the assays are shown in Table 1 below.

Two additional experiments were performed to examine the susceptibility of collagenase to surface denaturation. Collagenase was subjected to microscale drying without any surfactant, and the activity remaining was found to be 40.6±16.6%. This shows that the presence of surfactant (which shields the enzyme from surfaces) was critical, and supports the hypothesis that collagenase is very sensitive to surface denaturation. In addition, collagenase was deposited in reservoirs as 30 nL droplets and assayed without drying or lyophilizing, with 71±~10% activity remaining. This shows that the loss of activity was primarily due to the surface area, and not to capillary forces or freezing/sublimation damage.

The results with collagenase differed from the results with trypsin. First, the assay was less sensitive, leading to greater uncertainty in the data. Second, the bulk processes preserved the activity of the enzyme to a greater degree than either microscale process. It is thought that this occurred because collagenase (i) degrades relatively slowly in solution, making the process time constant less important; (ii) is very susceptible to denaturation at surfaces, making the increased surface area of the microscale process detrimental; and (iii) is more susceptible to capillary forces than freezing and sublimation damage, making lyophilization better than drying.

Example 3

Lyophilization and Drying of Elastase Solutions in a Microchip Reservoir

The in situ drying and lyophilization processes of Examples 1 and 2 were repeated with elastase in place of trypsin or collagenase. For elastase, the solution in Step 1 consisted of an aqueous solution containing 4 mg/mL elastase and 0.0005% Tween-20.

Elastase activity assays were performed using BZTA1aR [rhodamine 110, bis-(benzyloxycarbonyl-L-alanyl-L-alanyl-L-alanyl-alanine amide) dihydrochloride] as a substrate for the enzyme. The enzyme converts the BZTA1aR substrate into the fluorescent product rhodamine 110-benzyloxycarbonyl-L-alanyl-L-alanyl-L-alanyl-alanine amide. Solutions containing a fixed amount of substrate and a range of enzyme concentrations were prepared and allowed to react for 20 minutes. The fluorescence of each solution was measured and plotted as a function of enzyme concentration. The slope of this curve, as given by the best-fit straight line, is proportional to the enzyme activity.

The assay was performed on both unprocessed and processed enzyme, in order to compare the activity of the enzyme after processing to its activity pre-processing. The percent difference between the slopes of the two curves obtained is equivalent to the percent of enzyme activity lost as a result of the processing. Assays were performed in triplicate.

Each assay solution contained 20 mM calcium chloride, 10 mM tris(hydroxymethyl)aminomethane, 0.0005% (v/v) Tween-20, 18% (v/v) dimethylformamide, and 0.9 nM (nanomolar) BZTA1aR in a 2 mL aqueous solution at pH 8.80. The enzyme concentrations tested were 0, 1, 3, 6, 10, 30, 60, and 100 nM. The reaction was allowed to proceed at 25° C. for 20 minutes. Fluorescence was recorded using a fluorometer (Photon Technology International (PTI)) with a Xenon short-arc lamp, a photomultiplier tube (Products for Research Inc.), and a photomultiplier detector (PTI). The excitation and emission wavelengths were 492 and 523 nm, respectively.

The results with elastase are "intermediate" to the results from trypsin and collagenase. Although in this case the bulk lyophilization process preserved the activity of the enzyme to the greatest degree, the microscale processes were only slightly less effective, and bulk drying was by far the least effective method. It is thought that this occurred because elastase (i) degrades at a moderate rate in solution, making the process time constant important so that the three fastest processes are most effective and bulk drying, the slow process, is harmful and (ii) is susceptible to denaturation at surfaces, making the increased surface area of the microscale process a small disadvantage.

TABLE 1

Comparison of Enzyme Activity Following Processing

| Process | % Activity Remaining<br>Trypsin | Collagenase | Elastase |
|---|---|---|---|
| Bulk Drying | — | 88.3 ± 5.9 | 56.8 ± 1.0 |
| Microscale Drying | 88.0 ± 1.7 | 81.0 ± 13.5 | 74.2 ± 1.5 |
| Bulk Lyophilization | 77.0 ± 0.5 | 101.3 ± 5.7 | 84.1 ± 1.8 |
| Microscale Lyophilization | 74.3 ± 0.7 | 58.5 ± 10.1 | 77.1 ± 1.4 |

CONCLUSIONS FROM THE EXAMPLES

In the interpretation of this experimental data, several competing factors must be considered. There is degradation of the enzyme in the solution, denaturation at surfaces, damage due to capillary forces during drying, and damage due to freezing and sublimation. While a final protein formulation selected for use with known processes often involve a variety of additives and precisely controlled process parameters, the present experiments used only a small amount of surfactant to help prevent protein denaturation at surfaces. Other additives (e.g., lyoprotectants and/or cryoprotectants) or modification of process parameters could significantly improve the amount of enzyme activity preserved during processing.

Nonetheless, the most important factors in preserving the enzyme activity seem to be the process time constant and the surface area exposure. The balance between the enzyme's sensitivity to degradation in solution and its sensitivity to surface denaturation likely is critical. Addition of surfactants could prove to be effective in reducing the harmful effects of higher surface area on the microscale vs. bulk, whereas the time constant of a bulk process cannot be easily changed.

Note that the sensitivity of agents of interest to surface forces could be important when comparing this process to spray drying. Spray dried droplets are surrounded by air, while microscale deposited dried droplets are exposed to a solid surface and air. For aqueous protein solutions, the air/water interface is very hydrophobic and known to promote protein denaturation, while solid surfaces can be easily modified to be more hydrophilic. Moreover, the surface of the preselected site (for carrying out the drying or lyophilization) can be shaped, e.g., as in a reservoir, to minimize the air/water interface, as appropriate.

Modifications and variations of the methods and devices described herein will be obvious to those skilled in the art from the foregoing detailed description. Such modifications and variations are intended to come within the scope of the appended claims.

We claim:

1. A method of obtaining a quantity of a dry, solid form of an agent of interest comprising:

(a) providing a liquid which comprises an agent of interest dissolved or dispersed in a volatile liquid medium;

(b) depositing a microquantity of the liquid at a preselected site of a substrate; and (c) drying the microquantity of the liquid by volatilizing the volatile liquid medium to produce a dry, solid form of the agent of interest, wherein the volatile liquid medium comprises an aprotic, hydrophobic, non-polar liquid which comprises biocompatible perhalohydrocarbons or unsubstituted saturated hydrocarbons.

2. A method of obtaining a quantity of a dry, solid form of an agent of interest comprising:

(a) providing a liquid which comprises an agent of interest dissolved or dispersed in a volatile liquid medium;

(b) depositing a microquantity of the liquid at a preselected site of a substrate; and (c) drying the microquantity of the liquid by volatilizing the volatile liquid medium to produce a dry, solid form of the agent of interest, wherein the volatile liquid medium comprises one or more excipients, which comprise a surfactant.

3. The method of claim 2, wherein the surfactant comprises a polyoxyethylene sorbitan fatty acid ester.

4. The method of claim 2, wherein the microquantity of the liquid has a volume between 1 nL and 1 μL.

5. A method of obtaining a quantity of a dry, solid form of an agent of interest comprising:

(a) providing a liquid which comprises an agent of interest dissolved or dispersed in a volatile liquid medium;

(b) depositing a microquantity of the liquid at a preselected site of a substrate; and (c) drying the microquantity of the liquid by volatilizing the volatile liquid medium to produce a dry, solid form of the agent of interest, wherein the microquantity of the liquid has a volume between 10 nL and 500 nL, and wherein the agent of interest comprises an amino acid, a peptide, or a protein.

6. A method of obtaining a quantity of a dry, solid form of an agent of interest comprising:

(a) providing a liquid which comprises an agent of interest dissolved or dispersed in a volatile liquid medium;

(b) depositing a microquantity of the liquid at a preselected site of a substrate; and (c) drying the microquantity of the liquid by volatilizing the volatile liquid medium to produce a dry, solid form of the agent of interest, wherein the microquantity of the liquid is frozen after the deposition of step (b) and before the drying of step (c).

7. The method of claim 6, wherein the drying of step (c) comprises reheating the frozen microquantity.

8. A method of obtaining a quantity of a dry, solid form of an agent of interest comprising:

(a) providing a liquid which comprises an agent of interest dissolved or dispersed in a volatile liquid medium;

(b) depositing a microquantity of the liquid at a preselected site of a substrate; and (c) drying the microquantity of the liquid by volatilizing the volatile liquid medium to produce a dry, solid form of the agent of interest, wherein the drying of step (c) comprises subjecting the microquantity of the liquid to a sub-atmospheric pressure.

9. The method of claim 1, wherein the drying of step (c) is carried out at a temperature at or less than 10° C. at the preselected site.

10. A method of obtaining a quantity of a dry, solid form of an agent of interest comprising:

(a) providing a liquid which comprises an agent of interest dissolved or dispersed in a volatile liquid medium;

(b) depositing two or more discrete microquantities of the liquid at two or more discrete preselected sites of at least one substrate;

(c) drying the discrete microquantities of the liquid by volatilizing the volatile liquid medium to produce two or more microquantities of the dry, solid form of the agent of interest; and (d) combining together the two or more microquantities of the dry, solid form of the agent of interest to form a single collection of the dry, solid form of the agent of interest, wherein the agent of interest comprises insulin.

11. The method of claim 5, wherein step (b) comprises depositing two or more discrete microquantities at two or more discrete, preselected sites, respectively.

12. The method of claim 11, wherein each of the discrete, preselected sites is a microscale reservoir.

13. The method of claim 12, wherein the microscale reservoir is in the substrate of a microchip device.

14. The method of claim 12, wherein the microscale reservoir is located in a medical stent.

15. The method of claim 5, wherein the agent of interest comprises a pharmaceutical agent.

16. The method of claim 15, wherein the agent of interest further comprises one or more pharmaceutically acceptable excipients.

17. The method of claim 12, wherein the agent of interest comprises a pharmaceutical agent and the microscale reservoirs are provided in an implantable drug delivery device.

18. The method of claim 6, wherein step (b) comprises depositing two or more discrete microquantities at two or more discrete, preselected sites, respectively.

19. The method of claim 18, wherein each of the discrete, preselected sites is a microscale reservoir.

20. The method of claim 19, wherein the microscale reservoir is in the substrate of a microchip device.

21. The method of claim 19, wherein the microscale reservoir is located in a medical stent.

22. The method of claim 6, wherein the agent of interest comprises an amino acid, a peptide, or a protein.

23. The method of claim 6, wherein the agent of interest comprises a pharmaceutical agent.

24. The method of claim 23, wherein the agent of interest further comprises one or more pharmaceutically acceptable excipients.

25. The method of claim 19, wherein the agent of interest comprises a pharmaceutical agent and the microscale reservoirs are provided in an implantable drug delivery device.

26. The method of claim 19, wherein the microscale reservoir has a volume between 1 nL and 100 μL.

27. The method of claim 8 wherein step (b) comprises depositing two or more discrete microquantities at two or more discrete, preselected sites, respectively.

28. The method of claim 27, wherein each of the discrete, preselected sites is a microscale reservoir.

29. The method of claim 28, wherein the microscale reservoir is in the substrate of a microchip device.

30. The method of claim 28, wherein the microscale reservoir is located in a medical stent.

31. The method of claim 8, wherein the agent of interest comprises an amino acid, a peptide, or a protein.

32. The method of claim 8, wherein the agent of interest comprises a pharmaceutical agent.

33. The method of claim 32, wherein the agent of interest further comprises one or more pharmaceutically acceptable excipients.

34. The method of claim 28, wherein the agent of interest comprises a pharmaceutical agent and the microscale reservoirs are provided in an implantable drug delivery device.

35. The method of claim 28, wherein the microscale reservoir has a volume between 1 nL and 100 μL.

36. A method comprising:

(a) providing a liquid which comprises a pharmaceutical agent dissolved or dispersed in a volatile liquid medium;

(b) depositing two or more discrete microquantities of the liquid into two or more respective, discrete microreservoirs located in a medical stent; and (c) drying the two or more microquantities of the liquid by volatilizing the volatile liquid medium to produce dry, solid forms of the pharmaceutical agent in the microreservoirs of the medical stent.

37. The method of claim 36, wherein the liquid in step (a) further comprises one or more pharmaceutically acceptable excipients.

38. The method of claim 37, wherein the agent of interest comprises an amino acid, a peptide, or a protein.

39. The method of claim 36, wherein the microquantities of liquid are frozen after the deposition of step (b) and before the drying of step (c).

40. The method of claim 36, wherein the discrete microreservoirs are apertures extending through the medical stent.

* * * * *

UNITED STATES PATENT AND TRADEMARK OFFICE

CERTIFICATE OF CORRECTION

PATENT NO. : 7,354,597 B2
APPLICATION NO. : 11/308579
DATED : April 8, 2008
INVENTOR(S) : Audrey M. Johnson, et al.

It is certified that error appears in the above-identified patent and that said Letters Patent is hereby corrected as shown below:

At Column 1, Lines 15-16, delete “Grant No. 1-R24-AI47739-03 awarded by the National Institutes of Health,” and insert --grant number R24 AI047739 awarded by the NIH.--

Signed and Sealed this
Twenty-first Day of June, 2011

David J. Kappos
*Director of the United States Patent and Trademark Office*